(12) United States Patent
Wood et al.

(10) Patent No.: US 6,849,628 B2
(45) Date of Patent: Feb. 1, 2005

(54) OPTICALLY ACTIVE COMPOUNDS

(75) Inventors: Hamish Christopher Swan Wood, Glasgow (GB); Colin James Suckling, Glasgow (GB); Lilias Gilmour Rees, Glasgow (GB)

(73) Assignee: The University of Strathclyde, Glasgow (GB)

(*) Notice: Subject to any disclaimer, the term of this patent is extended or adjusted under 35 U.S.C. 154(b) by 252 days.

(21) Appl. No.: 10/228,820

(22) Filed: Aug. 27, 2002

(65) Prior Publication Data

US 2002/0198212 A1 Dec. 26, 2002

Related U.S. Application Data

(63) Continuation of application No. 08/426,458, filed on Apr. 18, 1995, now Pat. No. 6,500,829, which is a continuation of application No. 08/279,711, filed on Jul. 25, 1994, now abandoned, which is a continuation of application No. 08/127,414, filed on Sep. 27, 1993, now abandoned, which is a continuation of application No. 07/995,350, filed on Dec. 22, 1992, now abandoned, which is a continuation of application No. 07/869,902, filed on Apr. 15, 1992, now abandoned, which is a continuation of application No. 07/509,733, filed on Apr. 16, 1990, now abandoned, which is a division of application No. 07/403,917, filed on Sep. 1, 1989, now Pat. No. 4,959,472, which is a continuation of application No. 07/091,989, filed on Sep. 2, 1987, now abandoned.

(30) Foreign Application Priority Data

Sep. 3, 1986 (GB) .............................................. 8621268

(51) Int. Cl.[7] ............................................. A61K 31/519
(52) U.S. Cl. ...................................... 514/249; 544/258
(58) Field of Search ........................... 544/258; 514/249

(56) References Cited

U.S. PATENT DOCUMENTS

| 4,959,472 A | 9/1990 | Wood et al. ................. 544/258 |
| 5,010,194 A | 4/1991 | Mueller ....................... 544/258 |
| 5,134,235 A | 7/1992 | Mueller et al. ............. 544/258 |
| 5,347,005 A | 9/1994 | Mueller et al. ............. 544/258 |

FOREIGN PATENT DOCUMENTS

WO   WO 88/08844   11/1988

OTHER PUBLICATIONS

Rees et al., "Asymmetric Reduction of Dihydrofolate Using Dihydrofolate Reductase and Chiral Boron–Containing Compounds," *Tetrahedron*, vol. 42, No. 1, pp. 117–136, (1986).
Fontecilla–Camps et al., "Absolute Configuration of Biological Tetrahydrofolates. A Crystallographic Determination." *Journal of the American Chemical Society*, vol. 101, pp. 6114–6115 (Sep. 1979).
Temple et al., "Reversal of Methotrexate Toxicity in Mice by a Calcium Salt of Citrovorum Factor and Related Compounds," *Cancer Treatment Reports*, vol. 65, No. 11–12, pp. 117–119 (Nov./Dec. 1981).
Chello, et al., "Further Studies of Stereospecificity at Carbon 6 for Membrane Transport of Tetrahydrofolates, Biochemical Pharmacology", vol. 31, No. 8, pp. 1527–1530, 1981.
Kaufman, et al., "Chromatographic Separation of the Diastereoisomers of d 1.L–5, 10–Methylenetetrahydrofolate", *The Journal of Biological Chemistry*, vol. 238, No. 4, Apr. 1963, pp. 1498–1500.
Blair, John A., "Chemistry and Biology for Pteridines, Pteridines and Folic Acid Derivatives", *Proceedings of the Seventh International Symposium on Pteridines and Folic Acid Derivatives Chemical, Biological and Clinical Aspects*, St. Andres, Scotland, Sep. 21–24, 1982, p. 533.
Sirontnak, et al., "Stereospecificity at Carbon 6 o fFormyltetrahydrofolate As A Competitive Inhibitor of Transport and Cytotoxicity of Methotrexate in Vitro", *Biochemical Pharmacology*, vol. 28, pp. 2993–2997, 1979.
Straw, James A. et al., "Differences in the Pharmacokinetics of the Disastereoisomers of Citrovorum Factor in Dogs", *Cancer Research 41*, 3963–3939, Oct. 1981 and pp. 3936–3939, 3114–3119, Cancer Res. vol. 44 (1984).
J.C.S. Chem. Comm., 1974, pp. 175–176.
Machover, David, et al., "Treatment of Advanced Colorectal and Gastric Adenocarcinomas with 5–Fluorouracil and High–Dose Folinic Acid", *Journal of Clinical Oncology*, vol. 4, No. 5, pp. 685–696 (May), 1986.
Feeny, J., *Biochemistry*, vol. 20, p. 1837 (1981).
van Tamelen, et al., "Absolute Configuration of Biological Tetrahydrofolates, A Crystallorgraphic Determination", *Journal of American Chemical Society*/101:20/Sep. 26, 1979, pp. 6114–6115.
Kalbermatten, R., 266, "Uber Pterinchemie", *Helvetica Chimica Acta*, vol. 64, Fasc. 8 (1981), Nr. 266, pp. 2627–2635.
Blakely, R.L. et al., "Folates and Pterines", vol. 1, *Wiley Interscience*, (New York 1984).
Moran, R.G. Moran et al., "A simple Procedure for the Synthesis of High Specific Activity Triated (6S)–5–Formyltetrahydrofolate", *Analytical Biochemistry*, 122.70–78 (1982), p. 70–7.
Louslich, et al., *Journal Am. Chem. Soc.*, vol. 74, p. 4215–6 (1952).
Merck Index, 10th Ed. (1983), entry 4111.
Rees et al., *J. Chem Soc Chem. Comm.*, 1987, p. 470–2.

Primary Examiner—Richard L. Raymond
(74) Attorney, Agent, or Firm—Alston & Bird LLP

(57) ABSTRACT

The present invention relates to the preparation of substantially pure diastereoisomers of derivatives of tetrahydrofolate and the use of such diastereoisomers. More particularly the present invention provides a process for the preparation of a desired substantially pure (6R or 6S) diastereoisomer of a derivative of tetrahydrofolic acid or salt or ester. The process comprises the steps of: attaching a chiral auxiliary group at either N-5 or N-10 of a mixture of 6R and 6S diastereoisomers of tetrahydrofolic acid, separating the new diastereoisomers, recovering the desired new diastereoisomer (6R or 6S) corresponding to the desired (6R or 6S) diastereoisomer, and converting the substantially pure new diastereoisomer recovered into the corresponding diastereoisomer.

10 Claims, 3 Drawing Sheets

OPTICALLY ACTIVE COMPOUNDS

This application is a continuation of application Ser. No. 08/426,458, filed Apr. 18, 1995, now U.S. Pat. No. 6,500, 829, which a continuation of application Ser. No. 08/279, 711, filed Jul. 25, 1994, now abandoned, which is a continuation of application Ser. No. 08/127,414, filed Sep. 27, 1993, now abandoned, which is a continuation of application Ser. No. 07/995,350, filed Dec. 22, 1992, now abandoned, which is a continuation of application Ser. No. 07/869,902, filed Apr. 15, 1992, now abandoned, which is a continuation of application Ser. No. 07/509,733, filed Apr. 16, 1990, now abandoned, which is a division of application Ser. No. 07/403,917, filed Sep. 1, 1989 now U.S. Pat. No. 4,959,472, which is a continuation of application Ser. No. 07/091,989, filed Sep. 2, 1987, now abandoned.

The present invention relates to the preparation of substantially pure diastereoisomers of derivatives of tetrahydrofolate and the use of such diastereoisomers.

Methotrexate (N-(4-((2,4-diamino-6-pteridinyl) methyl) methylamino)benzoyl)-L-glutamic acid) is an inhibitor of the enzyme dihydrofolate reductase (DHFR) which prevents the conversion of deoxyuridylate into thymidylate. It thus prevents the biosynthesis of DNA and is commonly used in cancer chemotherapy. However, in common with most anti-cancer agents, it is toxic to normal cells as well as cancerous cells and hence a "rescue agent" is often administered some 12 to 24 hours after treatment with a high dose of methotrexate. Leucovorin (5-formyltetrahydrofolic acid) is the commonly used rescue agent for methotrexate.

Leucovorin has two chiral centres and the product commercially available (Wellcovorin (RTM) of the Wellcome Foundation Ltd) is composed of equal amounts of the compounds of formulae (Ia) and Ib) (in the form of their calcium salts) which compounds have the (R) and (S) stereochemistry respectively at C-6.

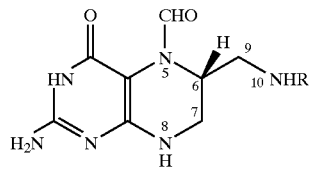
(Ia)

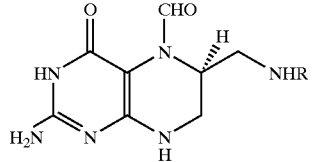
(Ib)

where

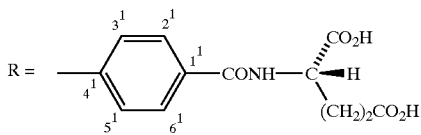

It has been reported (Montgomery et al, Cancer Treatment Reports, 1981, 65, 1117–1119) that only the (6S) diastereoisomer (Ib), which is the natural diastereoisomer, is effective in restoring one-carbon metabolism and thus of use in methotrexate rescue.

Indeed there are reports (Leary et al, Biochem, Biophys. Res. Commun., 1973, 56, 484) that thymidylate synthase from L. casei is inhibited by the non-natural diastereoisomer of 5,10-methylene tetrahydrofolate and that 5,10-methylene tetrahydrofolate dehydrogenase from E. coli is also inhibited by the same diastereoisomer (Scott and Donaldson, Biochem. Biophys. Res. Commun., 1964, 14, 523). Moreover, the non-natural diastereoisomer of 10-formyltetrahydrofolate is a potent competitive inhibitor of glycinamide ribonucleotide (GAR) formyl-transferase from chicken liver (Smith, Benkovic and Benkovic, Biochemistry, 1981, 20, 4034).

These results imply inhibition of both pyrimidine and purine biosynthesis, and thus of DNA biosynthesis also, by the non-natural diastereoisomers of one-carbon derivatives of tetrahydrofolate. If this inhibition is also present in mammalian systems there is a potential clinical requirement for the natural (6S) diastereoisomer of leucovorin.

Separation of the two diastereoisomers of leucovorin has been carried out by fractional crystallisation (Cosulich et al, J Amer.Chem.Soc, 1952, 74,4215) and by chromatography (Feeney et al., Biochemistry, 1981, 20, 1837) and the (6S) diastereoisomer has been obtained by the enzyme catalysed reduction of dihydrofolate followed by formylation (Rees, Valente, Suckling and Wood, Tetrahedron, 1986, 42, 117) but the yields are low in the latter and the isomers difficult to obtain in reasonable purity in the former. It is an object of the present invention to avoid or minimize one or more of the above disadvantages.

It has now been found that the introduction of a chiral auxiliary group into tetrahydrofolate or a tetrahydrofolate derivative close to the epimeric centre at C-6 enables ready separation of the new pair of diastereoisomers and the conversion of the separated diastereoisomers into pure (Ia) and (Ib) in good yield.

BRIEF DESCRIPTION OF THE INVENTION

FIG. 1 shows schematically the preparation of calcium 5-formyl-(6R and 6S) tetrahydrofolate (compounds 1a and 1b) via methyloxycarbonyl derivatives according to Example 1;

DETAILED DESCRIPTION OF THE INVENTION

Figure 1:
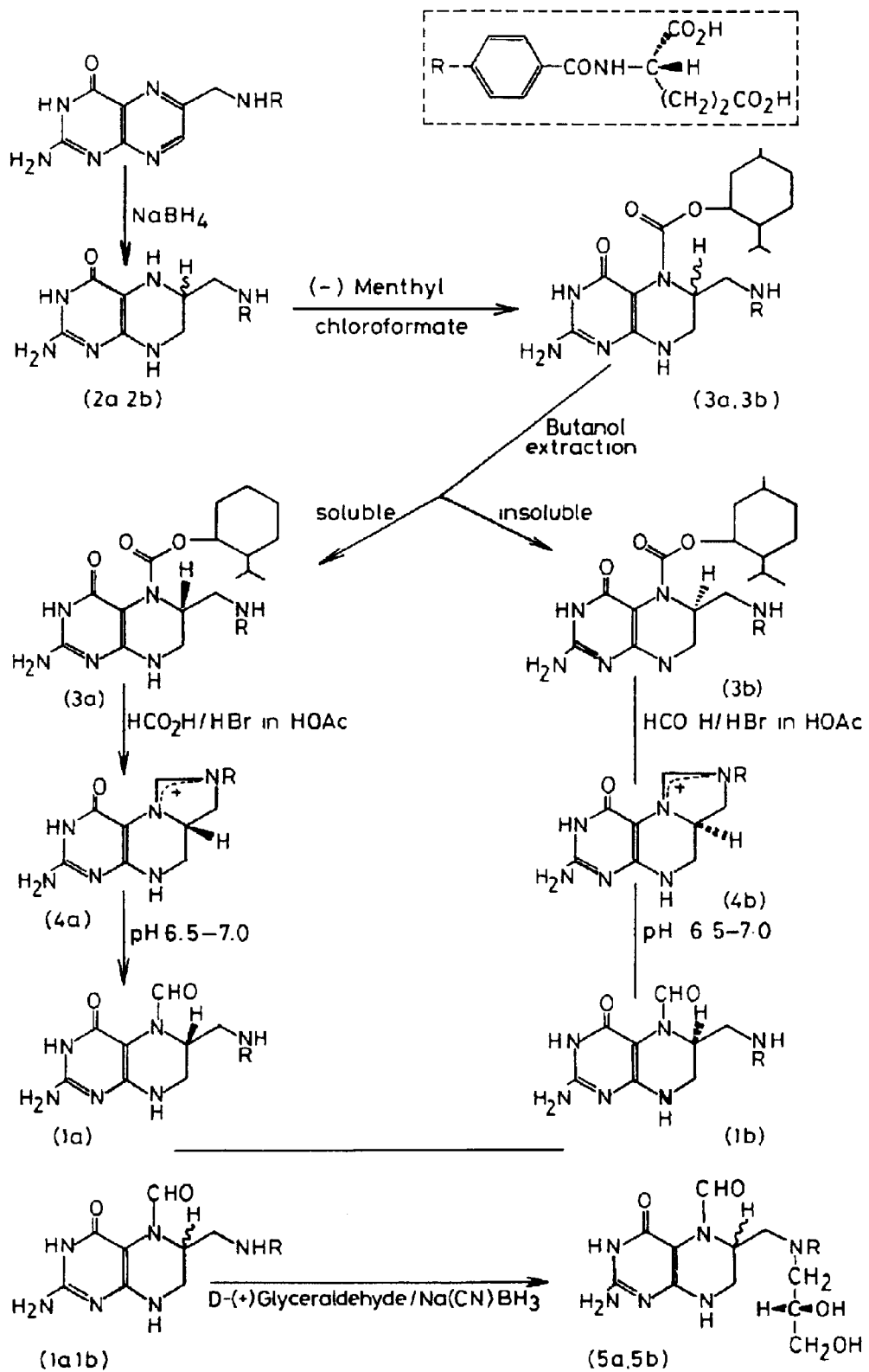
Figure 2:
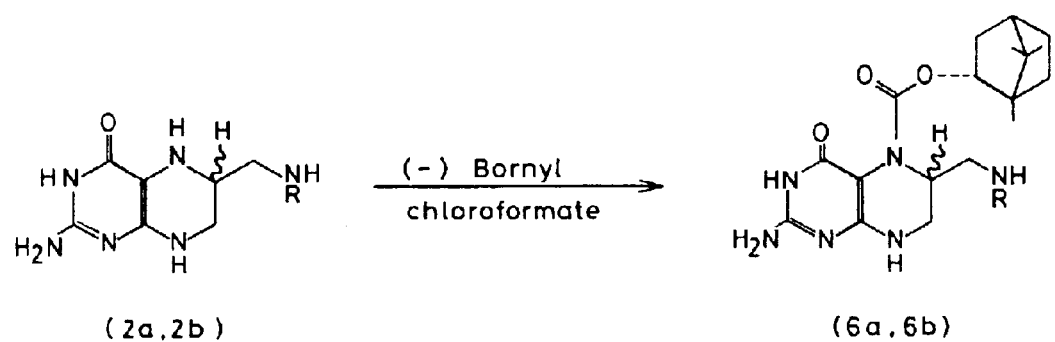
FIG. 2 shows schematically the formation of bornyloxycarbonyl derivatives according to Example 2.
Figure 3:
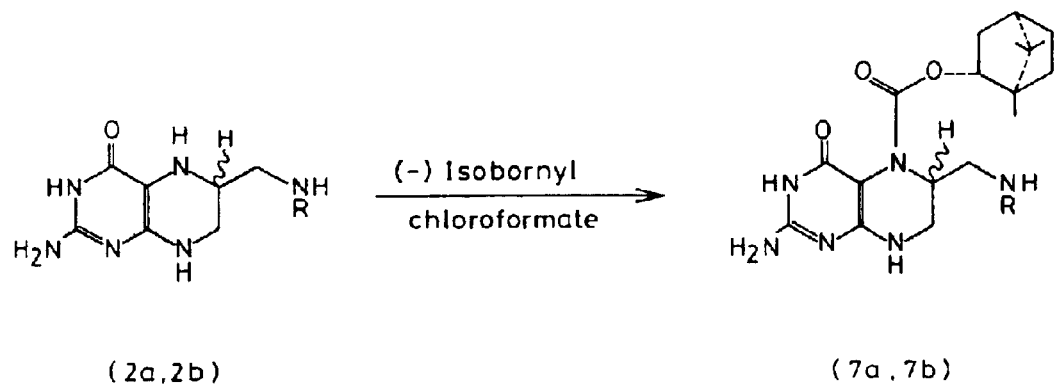
FIG. 3 shows schematically the formation of isobornyloxycarbonyl derivatives according to Example 3.
Figure 4:
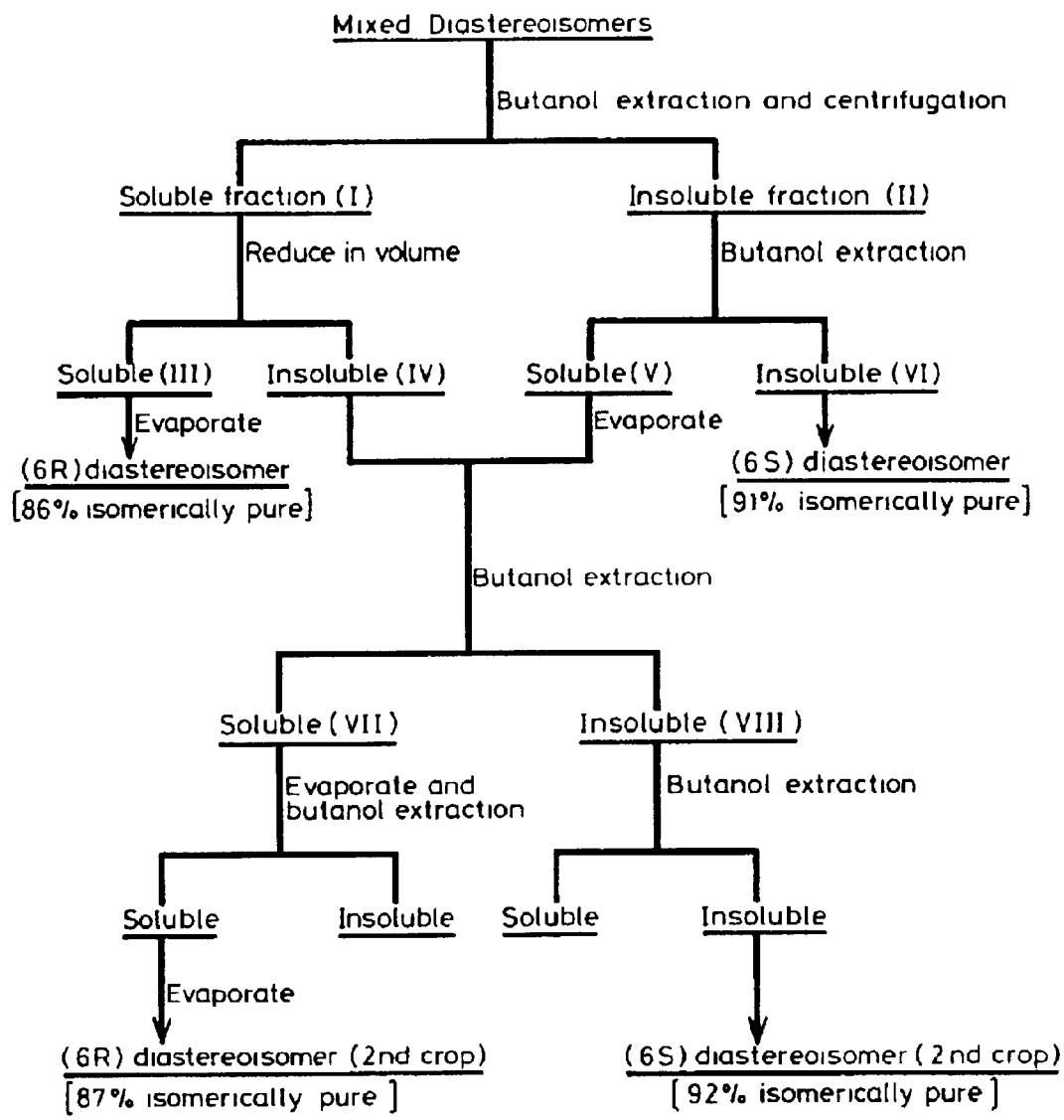
FIG. 4 shows schematically the separation of the mixed diastereoisomers (6RS) of 5-(−) methyloxycarbonyl-tetrahydrofolic acid (compounds 3a and 3b) according to Example 1(ii).

Accordingly, the present invention provides a process for the preparation of a desired substantially pure (6R or 6S) diastereoisomer of a derivative of tetrahydrofolic acid or a salt or ester thereof which process comprises the steps of: a) attaching a chiral auxiliary group at either N-5 or N-10 of a mixture of 6R and 6S diastereoisomers of tetrahydrofolic acid or of a substituted tetrahydrofolic acid, or salt or ester thereof, so as to form a pair of new diastereoisomers; b) separating the pair of new diastereoisomers and recovering the new diastereoisomer (6R or 6S) so formed corresponding to said desired (6R or 6S) diastereoisomer; and c) converting the substantially pure new diastereoisomer so isolated into the corresponding desired (6R or 6S) diastereoisomer of a derivative of tetrahydrofolic acid or salt or ester thereof.

Suitable derivatives of tetrahydrofolic acid and its salts and esters include leucovorin and 5-methyltetrahydrofolate, 5,10-methenyltetrahydrofolate and 5,10- methylenetetrahydrofolate. Leucovorin is a preferred derivative of tetrahydrofolate for the purposes of this invention.

For the avoidance of doubt it is noted that the present invention extends to both salts and esters of tetrahydrofolic acid. For the purposes of convenience though reference may be made herein simply to "tetrahydrofolate" or "substituted tetrahydrofolate" and unless the contrary is specifically indicated such references should be construed as including references to the free acid, and to salts and esters thereof. Particularly preferred are physiologically acceptable salts including calcium salts. Suitable esters include lower alkyl esters.

Chiral auxiliary groups may be introduced by standard methods known in the art, for example by the methods used for the protection of amino groups in peptide chemistry. Suitable chiral auxiliary groups are those which may be removed after separation of the pair of new diastereoisomers. It has been found that chiral alcohols in which the hydroxyl group is derivatised such that an urethane is formed on reaction with tetrahydrofolate are particularly convenient auxiliary groups. Substituted formate esters, for example chloroformate esters, of chiral alcohols such as (−) menthol, (−) borneol, (−) isoborneol (R) and
(S)-butan-2-ol, (S)-2-methylbutan-1-ol,
(R)-1-phenylpropan-1-ol, (R) and
(S)-2-methyl-1-phenylpropan-1-ol, (R) and
(S)-octan-2-ol, (R) and
(S)-1,2,3,4-tetrahydro-1-naphthol, (1S)-nopol,
(1S,2S,5S)-myrtanol, (1R)-myrtenol, (S)-B-citronellol, (−)-8-phenylmenthol, and (1S, 2R, 5R)-isomenthol are preferred reagents for attaching a chiral auxiliary group at N-5 of tetrahydrofolate. It has been found that when N-5 is unsubstituted reaction place at this position, otherwise reaction takes place at N-10. When reaction takes place at N-10, the substituent at N-5 should be the group attached to N-5 in the desired tetrahydrofolate derivative or convertible into such a group. Preferred groups at N-5 are formyl, methyl or groups convertible into formyl or methyl.

The reaction of chloroformate esters of chiral alcohols with a tetrahydrofolic acid conveniently takes place in a polar solvent, for example an aqueous solution of an alcohol such as ethanol at around neutral pH. The reaction can conveniently be carried out at a non-extreme temperature, for example, between −20 and 100° C. and suitably at room temperature.

The pair of new diastereoisomers so created may be separated by standard techniques such as crystallisation, chromatography, solvent extraction and similar methods. Solvents with which solvent extraction and recrystallisation may be effected include any suitable polar solvent. Preferably there is used an alcohol. Thus for example in the case of 5-(−) menthyloxycarbonyl-tetrahydrofolic acid the diastereoisomers may advantageously be separated by virtue of their different solubility characteristics in b"tan-1-ol. In the case of 5-(−) bornyloxycarbonyl-tetrahydrofolic acid the diastereoisomers may be advantageously separated by virtue of their different solubility characteristics in butan-1-ol or butan-2-ol. Where appropriate more than one solvent extraction or fractional crystallisation step may be carried out in order to improve purity. Conveniently the step may be repeated until the recovered new diastereoisomer has a purity greater than 90%.

The removal of the chiral auxiliary group from the separated diastereoisomers may be achieved by treatment with acid following the methods commonly used in peptide synthesis. Acids which may be used include mineral acids e.g. hydrobromic or sulphuric acid, organic acids, e.g. formic, acetic or trifluoroacetic acid or mixtures thereof. Thus, for example, the 5-(−)menthyloxycarbonyl or 5-(−) bornyloxycarbonyl derivatives of tetrahydrofolate may conveniently be treated with a mixture of formic acid and hydrogen bromide in acetic acid. Removal of the chiral auxiliary group in this way leads to the formation of individual diastereoisomers of 5,10-meth$^{en}$yltetrahydrofolate which may then be further converted into the desired derivative of tetrahydrofolate.

Thus, for example, individual diastereoisomers of 5,10-methenyltetrahydrofolate may readily be converted into the pure diastereoisomers of leucovorin at neutral pH, using methods known in the art, for example as described in British Patent No. 1560372. Alternatively the diastereoisomers of 5,10-methenyltetrahydrofolate may be converted into the individual diastereoisomers of 5-methyltetrahydrofolate for example by reduction with e.g. sodium borohydride in a manner similar to that described by Chanarin and Perry, *Biochem. J.* 1967, 105, 633.

Individual diastereoisomers of 5,10-methylenetetrahydrofolate may be prepared by cleaving the chiral auxiliary group from the separated intermediate diastereoisomers, for example in the presence of formaldehyde.

5,10-Methylenetetrahydrofolate may itself be converted into 5-methyltetrahydrofolate by reduction e.g. with sodium borohydride in a similar manner to that described by Sakami, *Biochem. Preparations*, 1963, 10, 103 and White, Bailey and Goldman, *J. Biol. Chem*, 1978, 253, 242.

When used herein the term "substantially pure" refers to the purity of a diastereoisomer of greater than 75%, preferably greater than 80% or 90%, and most preferably greater than 95%. The present invention also provides substantially pure diastereoisomers of tetrahydrofolate derivatives when prepared by the process described above. In a preferred embodiment the present invention also provides substantially pure diastereoisomers of leucovorin when prepared by the process described above. The purity of the diastereoisomers may be confirmed by reaction with D-glyceraldehyde in the presence of sodium cyanoborohydride and examination of the nmr spectra of the new diastereoisomers which are formed.

The intermediate compounds having a chiral auxiliary group attached at N-5 or N-10 of tetrahydrofolic acid or of a substituted tetrahydrofolic acid are novel compounds and as such form a further feature of the invention.

Preferred novel compounds according to this aspect are:
(6R) and (6S) 5-(−)menthyloxycarbonyl-tetrahydrofolic acid,
(6R)and (6S) 5-(−)bornyloxycarbonyl-tetrahydrofolic acid,
(6R) and (6S) 5-(−)-isobornyloxycarbonyl-tetrahydrofolic acid
as well as salts and esters thereof.

It will be appreciated that the novel intermediates possess a chiral centre at the 6-position of the pteridine ring and hence may exist in either the (6R) or (6S) isomeric form, or as a mixture of diastereoisomers.

The present invention further provides a-8-pharmaceutical composition comprising a substantially pure diastereoisomer of a derivative of tetrahydrofolate in combination with a pharmaceutically acceptable carrier. Suitable carriers include those known in the art for preparing pharmaceutical compositions containing leucovorin. In general the compositions of the present invention may be formulated similarly to previously known leucovorin compositions such as those commercially available under the trade name Wellcovorin (see for example Physician's Desk Manual, 1986, p.769, and Martindale "The Extra Pharmacopoeia" 26th Edition, page 1948). The substantially pure 6S diastereoisomer of leucovorin may be used as a rescue agent to counteract the action of DHFR inhibitors such as methotrexate. It may also be used in the treatment of folate deficiency. In addition it may be used in combination with 5-fluorouracil in the treatment of colorectal cancer (Machover et al, *Cancer Treatment Reports*, 1982, 66, 1803; Madajewicz et al, *Cancer Reasearch*, 1984, 44, 4667) and the present invention accordingly extends to its use in the preparation of medicaments for the treatment of such conditions and methods of treatment of such conditions in mammals. It is conveniently used in the form of a salt especially the calcium salt.

The substantially pure 6S-diastereoisomer of leucovorin may conveniently be administered orally or parenterally and may be formulated in conventional manner. Suitable formulations include injectible solutions; powders for injection, which may be reconstituted shortly before use by addition of Water for Injection; and tablets. When used as a methotrexate rescue agent dosage of the 6S diastereoisomer of leucovorin will depend inter alia on the amount of methotrexate administered; however a typical daily dose is generally up to 150 mg. e.g. in the range from 25 to 150 mg, which is conveniently administered in divided does, for example 2, 3 or 4 doses in a 24 hour period. For treating folate deficiency lower doses of leucovorin are generally administered. Thus, a typical daily dose for an adult human is generally in the range from 2 to 25 mg, which may conveniently be administered as a single dose, advantageously as a tablet. For treating colorectal cancer a typical daily dose for an adult human is generally in the range from 200 to 2000 mg p.d. together with from 200 to 2000 mg of 5-fluorouracil. 5-Methyltetrahydrofolate may be used as a dietary supplement.

The following examples, serve to illustrate the invention in a non-limiting manner and are illustrated in the attached Schemes.

In the Examples physical properties were measured as follows:
Nuclear Magnetic Resonance (nmr)
Recorded using a Bruker WH-250 spectrometer.
Tetramethylsilane was used as internal standard.
Optical Rotation
Specific rotations were determined using a Perkin Elmer 241 polarimeter with a 1 decimetre path length jacketed cell.

EXAMPLE 1

Preparation of Calcium 5-Formyl-(6R and 6S) Tetrahydrofolate Via Menthyloxycarbonyl Derivatives (i) Preparation of mixed diastereoisomers (6RS) of 5-(−) menthyloxycarbonyl-tetrahydrofolic acid (3a, 3b).

Folic acid (50 g) was suspended in distilled water (1050 ml) in a 10 litre three-necked flask equipped with a mechanical stirrer, a gas inlet and bubbler outlet for oxygen-free nitrogen, and a pressure equalising dropping funnel. The entire procedure which follows was carried out under nitrogen. The flask was surrounded by an ice-water bath and aqueous sodium hydroxide (50%; 21 ml) was then added followed by sodium borohydride (50 g) in water (150 ml) added dropwise over 30 minutes. The reaction mixture was stirred for 4.5 hours at 0–5° C. and then further sodium borohydride (50 g) in distilled water (150 ml) was added over 30 minutes. The mixture was stirred under nitrogen overnight. The reaction mixture was surrounded by an ice-water bath and the excess sodium borohydride was destroyed by dropwise addition of concentrated hydrochloric acid (175 ml) added over 45 minutes. Tris-hydrochloride buffer (50 mM, pH 7, 1 litre), which had been degassed and saturated with nitrogen, was added and the pH was adjusted to 7. A solution of (−) menthylchloroformate (30 ml) in ethanol (2.5 litres, degassed and saturated with nitrogen) was added in a single portion immediately after preparation of the solution, and the whole was left stirring at room temperature for 21.5 hours.

Using a rotary evaporator, the reaction mixture was reduced to half volume and filtered. The filtrate was kept cool in an ice-water bath and adjusted to pH3. The crude product which separated was collected by centrifugation and was purified by dissolving in aqueous sodium hydroxide (0.5 M; 1.5 litre), filtering and reprecipitating by adjusting to pH3 as before. The slurry was centrifuged and the solid was washed with a little water and filtered off. The solid was sucked dry and finally dried under vacuum over phosphorus pentoxide to give the mixed diastereoisomers of 5(−) menthyloxycarbonyl-tetrahydrofolic acid (88 g).

(ii) Separation of the mixed diastereoisomers (6RS) of 5-(−)menthyloxycarbonyl-tetrahydrofolic acid (3a and 3b)

The dry mixture of diastereoisomers (17 g) was stirred overnight with dry butan-1-ol (1.5 litres). The mixture was centrifuged to give a soluble fraction (I) and an insoluble fraction (II).

Using a rotary evaporator the soluble fraction (I) was reduced in volume to 400 ml at a temperature of 50–60° C. This resulted in formation of a new precipitate (IV) which was collected by centrifugation. The supernatant (III) was evaporated to dryness to give the menthyloxycarbonyl derivative of (6R) tetrahydrofolic acid (5.5 g). The precipitate (IV) was combined with a soluble fraction (V) obtained as described below.

The insoluble fraction (II) was stirred overnight with butan-1-ol (1 litre) in a second butanol extraction. This gave a soluble fraction (V) which was evaporated to dryness and used as described above, and an insoluble material (VI) which was dried over phosphorus pentoxide in vacuo to give the menthyloxycarbonyl derivative of (6S) tetrahydrofolic acid (5.47 g). Fractions (IV) and (V) were combined and stirred with butan-1-ol (300 ml) for 48 hours in a third butanol extraction. This again gave a soluble fraction (VII) and an insoluble fraction (VIII). The soluble fraction (VII) was evaporated to dryness using a rotary evaporator and the residue stirred overnight with butan-1-ol (35 ml). The soluble material was again evaporated to dryness to give a second crop of the menthyloxycarbonyl derivative of (6R) tetrahydrofolic acid (1.2 g).

The insoluble fraction (VIII) was stirred overnight with butan-1-ol (200 ml) and the resulting insoluble material was dried as above to give a second crop of the menthyloxycarbonyl derivative of (6S) tetrahydrofolic acid (1.2 g).

A diagrammatic representation of the separation process is given in Scheme 4.

(iii) Preparation of 5,10-methenyl-(6R) tetrahydrofolic acid chloride (NB: natural diastereoisomer) (4b)

5-(−)Menthyloxycarbonyl-(6S)tetrahydrofolic acid (40 g, 91% isomerically pure) was dissolved in formic acid (98%, 400 ml) in a 2-litre three-necked flask equipped with a gas inlet and outlet bubbler.

Hydrogen bromide in acetic acid (45%, 800 ml) was added. The reaction mixture was kept at 55–60° C. (bath) while hydrogen bromide gas was bubbled gently into the solution for 5 hours.

2-Mercaptoethanol (8 ml) was added and the reaction mixture was evaporated almost to dryness using a rotary evaporator at below 50° C. Hydrochloric acid (0.5 M, 1200 ml containing 0.1% of 2-mercaptoethanol) was added and the solution was warmed to 50° C. The warm solution was filtered and the filtrate reduced to about half its volume using a rotary evaporator at below 50° C. The mixture was refrigerated overnight and the yellow precipitate of 5,10-methenyl-(6R)tetrahydrofolic acid chloride (12.9 g) was collected by filtration and dried in vacuo over phorphorus pentoxide. Evaporation of the mother liquors gave further crops totalling 1.1 g.

(iv) Preparation of 5,10-methenyl-(6S)tetrahydrofolic acid chloride (NB: Unnatural diastereoisomer) (4a).

Prepared as above for the (6R) diastereoisomer using 5-(−)menthyloxycarbonyl-(6R)tetrahydrofolic acid (30.4 g) to give the title compound (17.6 g).

(v) Preparation of calcium 5-formyl-(6S) tetrahydrofolate (1b)

The entire procedure which follows was carried out under oxygen-free nitrogen. 5,10-Methenyl-(6R) tetrahydrofolic acid chloride (17.5 g) was added portionwise to stirred boiling water (400 ml) which had been previously degassed and saturated with nitrogen. After each addition the pH was adjusted to 6.5–7.0 with aqueous sodium hydroxide (3.7 M) which had also been degassed and saturated with nitrogen. The addition took about 45 minutes. The reaction was stirred under reflux with the pH being kept between 6.5 and 7.0 by addition of aqueous sodium hydroxide (3.7 M) for 5 hours.

The reaction mixture was allowed to cool overnight and the pH was adjusted to 9. Clarified calcium chloride solution (22 ml of a solution prepared by dissolving 10 g of anhydrous $CaCl_2$ in 25 ml of water) was added followed by ethanol (200 ml). The mixture was chilled, the cream coloured product was filtered off, washed with a little ethanol:water (50:50) and then with ethanol, and dried in vacuo over phosphorus pentoxide to give calcium 5-formyl-(6S)tetrahydrofolate (7.2 g), $[\alpha]_D^{20}$−12.5. Ethanol (500 ml) was added to the mother liquors to give further crops totalling 3.2 g.

(vi) Preparation of calcium 5-formyl-(6R) tetrahydrofolate (1a)

Prepared as above for the (6S) diastereoisomer using 5,10-methenyl-(6S)tetrahydrofolic acid chloride (17.5 g) to give the title compound (14 g), $[\alpha]_D^{20}$+22.9.

EXAMPLE 2

Preparation of Calcium 5-Formyl-(6R and 6S) Tetrahydrofolate Via Bornyloxycarbonyl Derivatives (i) Preparation of (−)Bornylchloroformate (−)Borneol (4.92 g) in dry toluene (30 ml) was added, dropwise over 1 hour, to phosgene in toluene (32 ml, 12.5%) in a round bottomed flask which was surrounded by an ice/water bath. The reaction mixture was allowed to come to room temperature and left tightly stoppered overnight.

The toluene was removed using an oil pump leaving a clear residue which was distilled (b.p.70° C. at 0.5 mm). (−)Bornylchloroformate was obtained as a white solid which had a strong carbonyl signal at 1770 $cm^{-1}$ and no hydroxyl signal in the infrared spectrum.

(ii) Preparation of mixed diastereoisomers (6RS) of 5-(−)bornyloxycarbonyl-tetrahydrofolic acid (6a,6b)

Folic acid (2.0 g) was reduced to tetrahydrofolic acid by the procedure used above for the preparation of menthyloxycarbonyl-tetrahydrofolic acid.

The reaction mixture was surrounded by an ice-water bath and the excess sodium borohydride was destroyed by dropwise addition of concentrated hydrochloric acid (6 ml). Tris-hydrochloride buffer (50 mM, pH7, 150 ml) which had been degassed and saturated with nitrogen, was added and the pH adjusted to 7. A solution of (−)bornylchloroformate (1.2 g) in ethanol (200 ml, degassed and saturated with nitrogen) was added in a single portion immediately after preparation of the solution, and the whole left stirring at room temperature for 2.25 hours. Using a rotatory evaporator, the reaction mixture was reduced to half volume and filtered. The filtrate was kept cool in an ice-water bath and adjusted to pH3. The crude product which separated was collected by centrifugation and was purified by dissolving in aqueous sodium hydroxide, filtering and reprecipitating by adjusting to pH3 as before. The slurry was centrifuged and the solid was washed with 100 ml water and filtered off. The solid was sucked dry and finally dried under vacuum over phosphorus pentoxide to give the mixed diastereoisomers of 5(−)bornyloxycarbonyl-tetrahydrofolic acid (2.42 g).

The diastereoisomers were separated as described above for the menthyloxycarbonyl derivatives using either butan-1-ol or butan-2-1. The separated diastereoisomers were converted into the diastereoisomers of calcium 5-formyltetrahydrofolate (Ia) and (Ib) as described for the menthyloxycarbonyl analogues.

EXAMPLE 3

Preparation of Calcium 5-formyl-(6R and 6S) Tetrahydrofolate Via Isobornyloxycarbonyl Derivatives (i) Preparation of (−)Isoborneol The reagent lithium tri(tertbutoxy)aluminium hydride was first prepared:

Lithium aluminium hydride (1.52 g) was suspended in dry ether (50 ml) and stirred. Dry t-butanol (8.89 g) in dry ether (10 ml) was added dropwise over 40 minutes. The mixture was then refluxed for 30 minutes.

Camphor (3.0 g) in dry ether (10 ml) was added dropwise to the refluxing reaction mixture over 30 minutes. The reaction mixture was refluxed for a further 2.25 hours. Water and aqueous hydrochloric acid were added to destroy excess reagent and the organic layer was separated and washed with water. The ethereal solution was dried over anhydrous sodium sulphate and evaporated using a rotary evaporator to give the white solid product (2.9 g). This was recrystallised from petroleum ether (b.p. 60–80° C.) to give a white crystalline solid, $[\alpha]_D^{20}$−29.0. GLC analysis (F.F.A.P. column at 120° C.) showed this to consist of 93.5% (−)isoborneol and 6.5%(+)borneol.

(ii) Preparation of (−)Isobornylchloroformate (−)Isoborneol (4.92 g) in dry toluene (20 ml) was added dropwise over 1 hour to phosgene in toluene (51.2 ml, 12.5%). The reaction mixture was left overnight in a round bottom flask which was equipped with a calcium chloride drying tube.

An infrared spectrum on a sample taken from the reaction mixture showed that the reaction was incomplete. Phosgene in toluene (26 ml, 12.5%) was added in a single portion and the flask was stoppered.

The reaction mixture was stirred at room temperature overnight. The toluene was removed under vacuum leaving the product as a thick oil which had a strong carbonyl signal at 1770 $cm^{-1}$ and no hydroxyl signal in the infrared spectrum.

(iii) Preparation of mixed diastereoisomers (6RS) of 5-(−) isobornyloxycarbonyl-tetrahydrofolic acid (7a,7b)

Folic acid (2.0 g) was reduced to tetrahydrofolic acid and the excess sodium borohydride was destroyed by the same procedure as used for the menthyloxycarbonyl-tetrahydrofolic acid preparation.

Tris-hydrochloride buffer (50 mM, pH7, 150 ml) which had been degassed and saturated with nitrogen was added and the pH adjusted to 7. A solution of (−)isobornylchloroformate (1.2 ml) in ethanol (200 ml, degassed and saturated with nitrogen) was added in a single portion immediately after preparation of the solution and the whole was left stirring at room temperature.

Hplc analysis showed that reaction was about 50% complete after 30 minutes. After a further 1.5 hours hplc analysis showed little change. A further addition of (−)isobornylchloroformate (1.2 ml) was made at this time and another addition an hour later. The whole was left stirring at room temperature overnight.

The product, an off-white precipitate, was filtered off and was purified by dissolving in aqueous sodium hydroxide, filtering, and reprecipitating by adjusting to pH3. The slurry was centrifuged and the solid was washed with a little water and filtered off to give the mixed diastereoisomers of 5(−)isobornyloxycarbonyl-tetrahydrofolic acid (1.45 g).

These diastereoisomers were separated by chromatography using preparative hplc on a reversed phase column and the purity of the separated diastereoisomers confirmed by analytical hplc.

This example illustrates the use of chromatographic separation of the 'new' diastereoisomers formed upon attachment of the chiral auxiliary group.

The separated 'new' diastereoisomers can then be converted into the corresponding diastereoisomers of tetrahydrofolic acid by the procedure of Example 1.

EXAMPLE 4

Preparation of Mixed Diastereoisomeric Derivatives of 5-Formyltetrahydrofolic Acid and Comparison of Physical Properties.

(i) Preparation of mixed diastereoisomers (6RS) of 5-formyl-10(2R,3-dihydroxypropyl) tetrahydrofolic acid (5a,5b)

The entire procedure which follows was carried out under oxygen-free nitrogen. Calcium 5-formyl-(6RS) tetrahydrofolate ("Wellcovorin", 0.1 g) was dissolved in distilled water (2 ml) and D(+) glyceraldehyde (0.071 g) and sodium cyanoborohydride (0.015 g) were added. The reaction mixture was stirred at room temperature and the pH was kept at about 5 by addition of hydrochloric acid (1M). After 24 hours and again after 48 hours, further additions of D(+) glyceraldehyde (0.071 g) and sodium cyanoborohydride (0.015 g) were made, the pH being maintained at 5 as before. After 70 hours the pH was adjusted to 3 and the solution was chilled to give the mixed diastereoisomers (0.016 g) as a light coloured solid. The nmr spectrum of the mixture showed characteristic peaks for the 5-formyl group at 8.71 and 8.80 ppm.

Prepared similarly were the corresponding derivatives of 5-formyl-(6S)-tetrahydrofolic acid (prepared as described in Example I(v)above and from a sample of tetrahydrofolate prepared by enzymic reduction of dihydrofolate) and of the (6R) diastereoisomer. The derivatives could be distinguished by their nmr spectra as follows:

(a) Derivative (5b) of (6S) Diastereoisomer
  (i) Diastereoisomer prepared in Example 1(v) above. Signal at 8.71 ppm.
  (ii) Diastereoisomer prepared enzymatically. Signal at 8.71 ppm.
(b) Derivative (5a) of (6R) Diastereoisomer Prepared in Example 1 (vi) Above. Signal at 8.80 ppm.

What is claimed is:

1. A pharmaceutical composition for therapeutic use which consists essentially of a therapeutically effective amount, sufficient for the treatment in conjunction with 5-fluorouracil of human beings for colorectal cancer, of a pharmaceutically acceptable compound which is a (6S) diastereoisomer selected from the group consisting of (6S) leucovorin (5-formyl-(6S)-tetrahydrofolic acid) and pharmaceutically acceptable salts and esters of (6S) leucovorin; wherein the compound consists of a mixture of (6S) and (6R) diastereoisomers and consists of at least 92% by weight of the (6S) diastereoisomer, the balance of said compound consisting of the (6R) diastereoisomer; in combination with a pharmaceutically acceptable carrier; and in conjunction with a therapeutically effective amount of 5-fluorouracil.

2. The pharmaceutical composition according to claim 1 which consists essentially of about 92% by weight of the (6S) diastereoisomer.

3. The pharmaceutical composition according to claim 1 which consists essentially of 92% to 95% by weight of the (6S) diastereoisomer.

4. The pharmaceutical composition according to claim 1 which consists of greater than 95% by weight of the (6S) diastereoisomer.

5. The pharmaceutical composition according to claim 1 which consists essentially of 200 to 2000 mg of the mixture of (6S) and (6R) diastereoisomers.

6. The pharmaceutical composition according to claim 1 wherein the 5-fluorouracil is present in a therapeutically effective amount of 200 to 2000 mg.

7. The pharmaceutical composition according to claim 1 wherein the mixture of (6S) and (6R) diastereoisomers is present in the composition in an amount of at least about 10 grams.

8. The pharmaceutical composition according to claim 1 the form of divided doses.

9. The pharmaceutical composition according to claim 1 wherein said composition is present in a form selected from the group consisting of injectable solutions, powders for injection which can be reconstituted shortly before use by addition of water for injection, and tablets.

10. The pharmaceutical composition according to claim 1 wherein the mixture of (6S) and (6R) diastereoisomers is produced as a result of separation by differential solubility in a polar solvent of a (6S) diastereoisomer from an initial mixture containing equal amounts of (6S) and (6R) diastereoisomers.

* * * * *